United States Patent
Brooks

[19]

[11] Patent Number: 5,150,708
[45] Date of Patent: Sep. 29, 1992

[54] TABBED DEFIBRILLATOR ELECTRODE PAD

[75] Inventor: Robert J. Brooks, Everett, Wash.

[73] Assignee: SpaceLabs, Inc., Redmond, Wash.

[21] Appl. No.: 621,863

[22] Filed: Dec. 3, 1990

[51] Int. Cl.⁵ .............................. A61N 01/04
[52] U.S. Cl. ................... 128/419 D; 128/640
[58] Field of Search ............... 128/419 D, 640–641, 128/798, 802–803; 606/32

[56] References Cited

U.S. PATENT DOCUMENTS

| | | | |
|---|---|---|---|
| 3,599,629 | 8/1971 | Gordy | 128/640 |
| 4,524,087 | 6/1985 | Engel | 128/802 |
| 4,559,950 | 12/1985 | Vaughan et al. | 128/803 |
| 4,653,501 | 3/1987 | Cartmell et al. | 128/640 |
| 4,768,514 | 9/1988 | De Marzo | 128/640 |
| 4,777,954 | 10/1988 | Keuch et al. | 128/641 |
| 4,779,630 | 10/1988 | Scharnberg et al. | 128/798 |
| 4,798,208 | 1/1989 | Faasse, Jr. | 128/640 |
| 4,827,939 | 5/1989 | Cartmell et al. | 128/640 |
| 4,838,273 | 6/1989 | Cartmell | 128/802 |
| 4,852,571 | 8/1989 | Gadsby et al. | 128/640 |
| 4,899,754 | 2/1990 | Bly et al. | 128/640 |
| 4,955,381 | 9/1990 | Way et al. | 128/419 D |

Primary Examiner—Lee S. Cohen
Assistant Examiner—J. R. Jastrzab
Attorney, Agent, or Firm—Seed and Berry

[57] ABSTRACT

A defibrillator electrode pad for conducting electricity between the body of a patient includes a flexible backing having an application surface upon which is mounted a metallic electrode. An adhesive is disposed upon the electrode and a portion of the application surface of the flexible backing. A gripping tab includes a first portion fixed to the flexible backing and a second portion integral with the first portion and projecting outward from the flexible backing. The second portion of the gripping tab includes a gripping surface made of a material selected to prevent the adhesive from sticking to the gripping surface. A paper release sheet is constructed to be applied to the application surface of the backing to prevent the adhesive from unintentionally sticking to objects. The paper release sheet includes a tab portion constructed to project outward from the flexible backing.

26 Claims, 2 Drawing Sheets

TABBED DEFIBRILLATOR ELECTRODE PAD

TECHNICAL FIELD

The present invention is directed toward electrode pads, and more particularly, toward defibrillator pads including an extending tab portion for enabling a user to easily handle the pad.

BACKGROUND OF THE INVENTION

Defibrillator systems for providing electrical stimuli to a patient to reactivate the patient's heart pumping activity typically include electrode pads that are electrically coupled to the patient for transmitting the electrical stimuli to the patient's body. These same electrode pads can also be used for: continuous cardiac electrical stimulation such as used in pacemakers; continuous electrical monitoring of heart activity commonly referred to as electrocardiogram (ECG) monitoring; plethysmography such as used in measuring the impedance of a patient; or other electrical monitoring of the patient or therapeutic delivery of electrical signals to the patient.

Preferably, the electrode pad includes a metallic electrode adapted to cover a relatively large surface area on the patient's body to minimize the concentration of electricity provided to the patient's skin and thereby minimize electrical burning. Further, these electrode pads preferably include a material, such as a conductive polymer, for increasing the conductivity between the electrode of the electrode pad and the body of the patient. Improved electrode pads have been provided with an adhesive substance adapted to adhere the electrode pad to the patient's body, thereby to insure good electrical contact between the electrode pad and the patient's body and, further, to free the hands of the operator. Prior electrode pads further include a paper backing that is disposed over the adhesive to prevent the electrode pad from unintentionally adhering to objects other than a patient's body at times when the electrode pad is not in use.

Prior art electrode pads have failed, however, to provide a means for convenient handling of the electrode pads. With particular regard to adhesive-covered electrode pads, the prior art have failed to provide means for enabling ready-handling of the electrode pads by the user such that the user is not required to contact the adhesive of the pad. This failure of prior art electrode pads is particularly disadvantageous to the user who is required to handle the electrode pads while wearing rubber gloves that have become commonplace in the medical industry. Since rubber gloves tend to exhibit greater adhesion to the adhesive of the electrode pad than the skin of the operator, manipulation of prior art electrode pads with rubber gloves is particularly difficult.

More particularly, prior art electrode pads have failed to provide any means for enabling a user to readily remove the paper release sheet without contacting the adhesive of the electrode pads. Further, prior art electrode pads have failed to provide any mechanism for allowing the user to easily apply the electrode pads to the patient's body without contacting the adhesive thereof. Still further, prior art electrode pads have failed to provide any means for enabling a user to readily remove the electrode pads from the patient. Prior art electrode pads have also failed to provide means for manipulating the electrode pads adhered to the patient's body.

Accordingly, it is a primary object of the subject invention to overcome these limitations of the prior art. Other objects and advantages of the subject invention will become apparent from a reading of the following detailed description of the invention taken in conjunction with the drawings.

SUMMARY OF THE INVENTION

The subject invention is directed toward an improved electrode pad wherein the electrode pad includes a substantially flexible backing upon which is mounted the defibrillator electrode. An adhesive is disposed upon the flexible backing and electrode for adhering the electrode pad to a patient. A gripping portion is securably attached to the flexible backing and constructed to project therefrom thereby to provide a gripping edge to the user.

In a particularly preferred embodiment of the invention, the defibrillator pad includes a release sheet that is constructed to mate substantially with the flexible backing. The release sheet includes an extending portion that is constructed and positioned to substantially mate with the gripping portion of the flexible backing, for providing a gripping edge to the user for removal of the release sheet. Preferably, in addition to being constructed and positioned to substantially mate with the gripping portion of the flexible backing, the extending portion of the release sheet is made slightly larger than the projecting portion of the electrode pad thereby to allow the release sheet to be easily gripped and separated from the electrode pad by pulling the extending portion of the release sheet in a direction opposite to that of the gripping portion of the electrode pad.

DETAILED DESCRIPTION OF THE INVENTION

Figure 1:
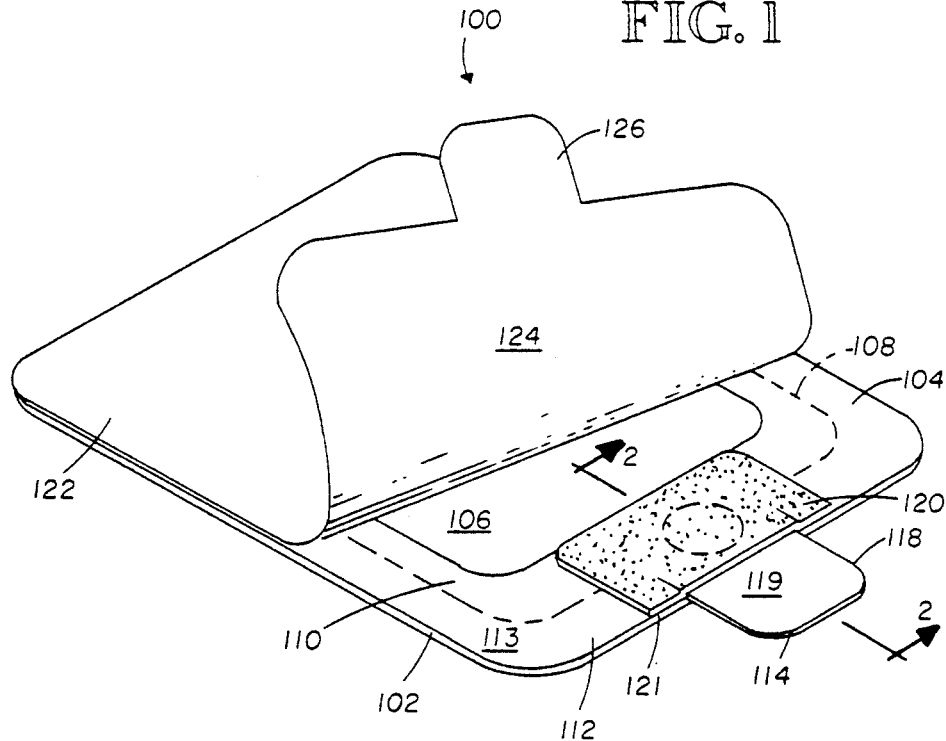
FIG. 1 is an isometric view of a presently preferred embodiment of the electrode pad that is the subject of this invention.

An improved defibrillator electrode pad 100, illustrated in FIG. 1, includes a backing 102. The backing 102 is constructed of generally rectangular shape and has a thickness that is selected to allow the backing to be substantially flexible. In the presently preferred embodiment of the invention, the backing is constructed of foam. However, those skilled in the art will recognize that many materials and shapes may be substituted for the foam backing of the subject invention. Preferably, the backing 102 will be constructed of a material which is a flexible insulator material.

The backing 102 includes an application surface 104 upon which is mounted an electrode 106. As is known in the art, the electrode 106 is provided for conducting electricity from a defibrillator to the body of a patient. To maximize the amount of electricity that is conducted to the patient's body, while simultaneously minimizing electrical burn to the skin of the patient, the electrode 106 is generally constructed to cover a significant area on the patient's body. Typically, the electrode 106 may be between 10 and 15 square inches in surface area. Those skilled in the art will recognize, however, that the electrode 106 may be made somewhat smaller or larger than the presently preferred dimensions without departing from the true scope of the subject invention.

The electrode 106 is preferably constructed of a metal, or other material, that is substantially electrically conductive for conducting electricity to the body of the patient. Further, the electrode 106 is constructed of a thickness so that the electrode is substantially flexible. In the presently preferred embodiment of the invention, the electrode 106 is constructed from a thin layer of tin. Those skilled in the art will recognize, however, that other materials and constructions for the electrode 106 are possible.

As illustrated in FIG. 1, the electrode 106 is mounted to the application surface 104 of the backing 102. The electrode 106 may be mounted to the backing 102 in any conventional manner. In the presently preferred embodiment of the invention, the electrode 106 is mounted to the backing 102 with a conventional adhesive layer 200 (FIG. 2) that is disposed over the entire application surface 104 of the backing 102.

With further reference to FIG. 1, it is noted that the electrode 106 is constructed of a shape substantially similar to the shape of the backing 102 and has a surface area that is smaller than the surface area of the backing 102. The electrode 106 is positioned substantially in the center of the backing 102 such that an adhesive portion 108 of the application surface 104 of the backing 102 extends beyond the periphery of the electrode 106.

Figure 2:
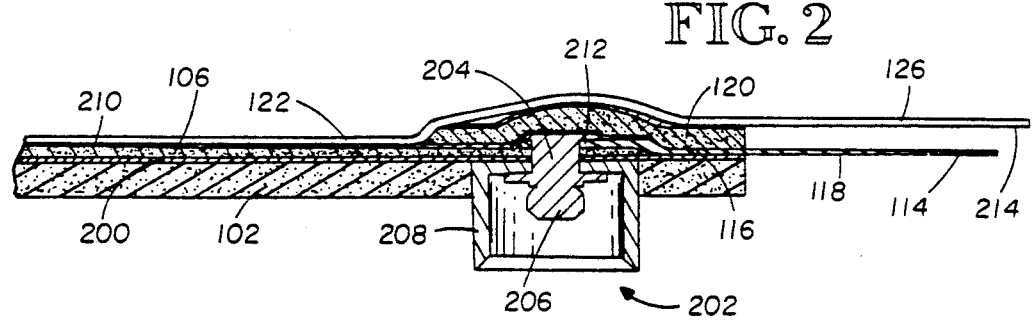
FIG. 2 is a cross-sectional view along lines 2—2 of FIG. 1.

A connector 202, best illustrated in FIG. 2, is mechanically coupled to the backing 102. The connector 202 is provided for electrically coupling the electrode pad 100 to a cable of the defibrillator so that electrical signals may be transmitted between the defibrillator and the electrode pad 100. The connector 202 includes a stem 204 that extends through the backing 102 for making electrical contact to the electrode 106. The stem 204 is constructed of an electrically conductive metal and includes a coupling portion 206 that is constructed to mate with a coupling portion of the defibrillator cable. The connector 202 further includes a receiving clip 208 that is constructed to receive the coupling portion of the defibrillator cable and to grip and hold the defibrillator cable coupling portion thereby to maintain electrical contact between the stem 204 and the defibrillator cable. The stem 204 also includes a crimping portion 212 adapted to crimp the stem 204 to the backing 102 and the electrode 106 thereby enhancing the stability of the mechanical coupling between the connector 202 and the electrode pad 100. Those skilled in the art will recognize that additional fastening elements, such as conductive and non-conductive washers, may be added to the mechanical coupling between the connector 202 and the backing 102 to provide greater stability of the mechanical coupling and prevent the connector 202 from separating from the backing 102.

A second adhesive 210 (FIG. 2) is disposed over the electrode 106 for adhering the electrode 106 to the body of the patient. Preferably, the adhesive 210 is a conductive adhesive that is disposed upon the electrode 106 and extends outwardly beyond the periphery of the electrode 106 to cover a first portion 110 of the adhesive portion 108 of the backing 102 (FIG. 1). In the presently preferred embodiment of the invention, the conductive adhesive 210 is composed, at least in part, of a conducting material thereby to enable the conductive adhesive 210 to conduct electricity between the electrode 106 and the patient's body. Those skilled in the art will understand that it may be desired to alter the degree of conductivity of the adhesive 120 to make it more or less conductive than is desirable for defibrillator application. Further, the conductive adhesive 210 is composed of a material to make the conductive adhesive removably adherable to the body of a patient.

In the presently preferred embodiment of the invention, the conductive adhesive 210 is composed of a conducting polymer, or a semiconducting polymer, that is present in the conductive adhesive 210 in a sufficient amount to make the conductive adhesive 210 both substantially electrically conducting and sticky. The conductive adhesive 210 is presently being supplied by Katecho, Inc. of Des Moines, Iowa, although other suppliers of suitable conductive adhesives may be found. Those skilled in the art will be able to develop alternative conductive adhesives that include an effective amount of a conducting polymer to make the conductive adhesive both substantially electrically conductive and sticky. Further, it will be apparent to those skilled in the art that other compositions may be substituted for the conductive adhesive 210 without departing from the true scope of the invention.

The first portion 110 of the application surface 104 of the backing 102 does not extend completely to the periphery of the backing 102 but, instead, extends partway beyond the periphery of the electrode 106 to the periphery of the backing 102 such that the conventional adhesive 200 that is disposed upon the application surface 104 of the backing 102 is exposed between the periphery of the conductive adhesive portion 110 and the periphery of the backing 102. The conventional adhesive 200 may comprise an adhesive that is disposed upon the application surface 104 of the backing 102 for removably adhering the backing 102 to the body of the patient. Those skilled in the art will readily recognize that many known adhesives may be used for this purpose. It will be apparent to those skilled in the art that the conductive adhesive 210 and the conventional adhesive 200 cooperate to removably adhere the electrode pad 100 to the patient's body.

A gripping tab 114 includes a mounting portion 116 and a projecting portion 118. The gripping tab is provided to enable a user to easily manipulate the electrode pad 100 without contacting the conductive adhesive 210 or the conventional adhesive 200. The mounting portion 116 is fixedly mounted to the adhesive portion 108 of the application surface 104 of the backing 102. In an alternative embodiment, the stem 204 of the connector 202 may be constructed to extend through the mounting portion 116 of the gripping tab 114 such that the crimping portion 212 further grips and fixedly mounts the gripping tab 114 to the backing 102.

In the presently preferred embodiment of the invention, the gripping tab 114 is positioned in the center of a first edge 121 of the backing 102. Central positioning of the gripping tab 114 is preferred to improve the ease with which the electrode pad 100 is manipulated by a user. It will be apparent, however, to those skilled in the art, that the gripping tab 114 may be positioned anywhere along the first edge 121 of the electrode pad 102 without departing from the true scope of the subject invention.

The projecting portion 118 of the gripping tab 114 extends beyond the periphery of the backing 102 and provides a gripping edge for the user. In the presently preferred embodiment of the invention, the mounting portion 116 is fixed to the backing 102 by the conventional adhesive 200. Those skilled in the art will recognize that other means for securing the gripping tab 114 to the backing 102 may be employed or alternatively the gripping tab 114 could be integral with backing 102. The projecting portion 118 includes a gripping surface 119 that is constructed with a generally rectangular shape and is sized to be readily gripped by a user of the electrode pad 100. More particularly, the gripping surface 119 of the projecting portion 118 is sized to be gripped between the thumb and index finger of a user for manipulation of the electrode pad 100 by the user's fingers. The gripping surface 119 is preferably constructed of a material selected to substantially prevent adhesion of the conventional adhesive 200 and the conductive adhesive 210 to the projecting portion 118. Further, the gripping tab 114 is preferably constructed of a substantially flexible material that is also tough enough to prevent tearing or breakage of the gripping tab 114. In the presently preferred embodiment of the invention, the gripping tab 114 is constructed from vinyl.

A reinforcing pad 120 is mounted upon the mounting portion 116 of the gripping tab 114 by the conventional adhesive 200. The reinforcing pad 120 is provided for reinforcing the mechanical coupling between the connector 202, the backing 102, and the gripping tab 114. Further, the reinforcing pad 120 provides electrical isolation between the stem 204 and crimping portions 212 of the connector 202 and the body of the patient. A portion of the conventional adhesive 200 is disposed upon the reinforcing pad 120 so that the reinforcing pad 120 will adhere to the body of the patient.

A paper release sheet 122 is constructed of generally rectangular shape and is sized to mate with the backing 102. The paper release sheet is provided for covering the conductive adhesive 210 and the conventional adhesive 200 thereby to prevent the electrode pad 100 from adhering to objects other than a patient's body while the electrode pad 100 is not in use. The paper release sheet 122 includes a first surface 124 that is adapted to be positioned proximate the conductive adhesive 210 and the conventional adhesive 200. The first surface 124 is covered with a material to allow the paper release sheet 122 to be readily removed from the electrode pad 100. In the presently preferred embodiment of the invention, the first surface 124 of the paper release sheet 122 is covered with wax. Other materials for the first surface 124 will readily become apparent to those skilled in the art.

The paper release sheet 122 includes a tab portion 126 that is constructed to extend beyond the periphery of the backing 102. The tab portion 126 of the paper release sheet 122 is constructed and positioned to substantially mate with the gripping tab 114. Preferably, in addition to being constructed and positioned to substantially mate with the gripping tab 114, the tab portion 126 includes an extending portion 214 (FIG. 2) that extends slightly beyond the gripping tab 114 to provide a gripping edge to the user for easy separation of the tab portion 126 from the tripping tab 114. In operation, the paper release sheet 122 is readily removed from the electrode pad 100 by simultaneously gripping the tab portion 126 and the gripping tab 114 and pulling in opposite directions. It will be apparent to those skilled in the art that although the invention is described by reference to a tab portion 126 that is constructed to extend slightly beyond the gripping tab 114, such construction is not essential to the operation of the invention. The tab portion 126 may be made slightly smaller than the gripping tap 114 or even substantially the same size as the gripping tab 114. Further, it will be apparent to those skilled in the art that although the paper release sheet 122 is constructed from paper in the presently preferred embodiment of the invention, other materials may be readily substituted therefor.

The electrode pad 100 that has been described by reference to FIGS. 1 and 2 may be readily manipulated by a user by gripping the projecting tab 114. Examples of the uses to which the gripping tab 114 may be put while manipulating the electrode pad 100 include use to remove the release sheet 122 prior to the application of the electrode pad 100 to the body of a patient, as discussed above. Further, the gripping tab 114 may be used to hold the electrode pad 100 while the pad is being positioned and pressed down upon the patient's body. Still further, the gripping tab 114 provides a convenient gripping edge for removing the electrode pad 100 from the patient's body after the defibrillation is completed. At times when the cable of the defibrillator is unintentionally disconnected from the connector 202 during use of the electrode pad 100, the gripping tab 114 can be used to facilitate reconnection of the defibrillator to the connector 202.

Figure 3:
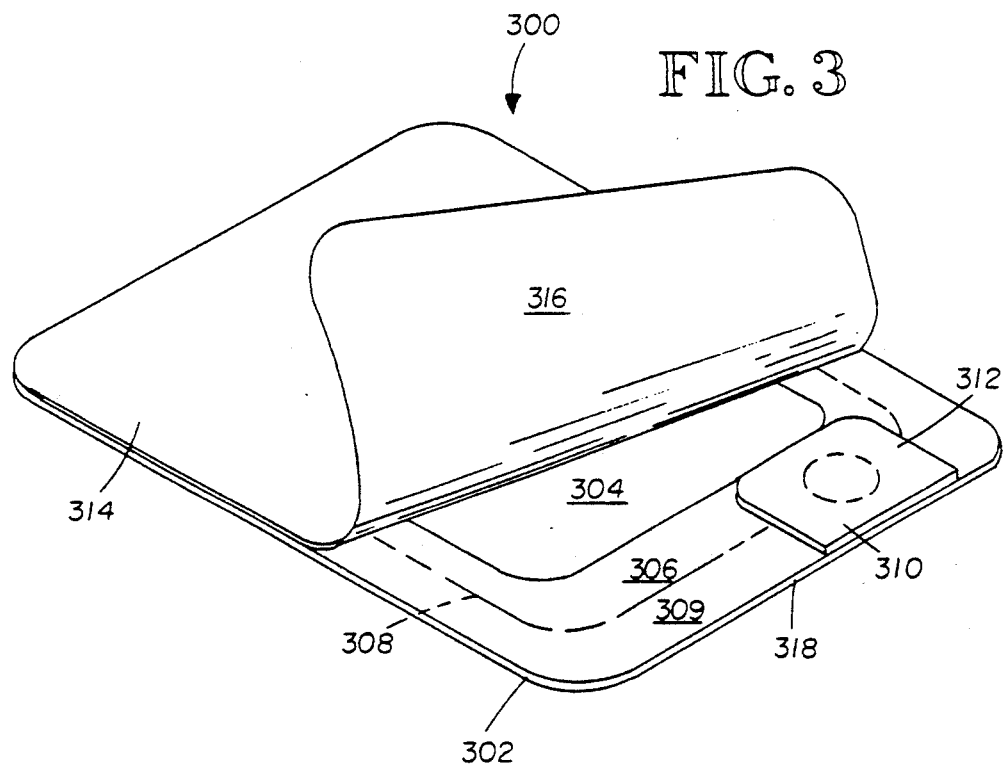
FIG. 3 is an isometric of an alternative embodiment for the electrode pad that is the subject of this invention.

An alternative embodiment of the subject invention is illustrated in FIG. 3 wherein an electrode pad 300 includes a backing 302 upon which is mounted a electrode 304. A conductive adhesive 306 is disposed upon the electrode 304 and extends beyond the periphery of the electrode 304 into an adhesive portion 308 of the surface of the backing 302. A conventional adhesive 309 is disposed upon the surface of the backing 302 intermediate the periphery of the conductive adhesive 306 and the periphery of the backing 302. A gripping pad 310 is mounted upon the adhesive portion 308 of the backing 302. The gripping pad 310 is positioned to cover a conductor (not shown) of the electrode pad 300 thereby to provide electrical isolation between the conductor and the body of the patient. The gripping pad 310 includes an exposed surface 312 positioned to face outwardly of the backing 302. The exposed surface 312 is preferably covered with a material that is substantially non-adhesive. As an example, the exposed surface of the gripping pad 310 may be covered with wax as discussed above by reference to the paper release sheet 122 of the electrode pad 100. Alternatively, vinyl or other non-adhering materials may be positioned on the exposed surface 312 of the gripping pad 310. A paper release sheet 314 includes a waxed surface 316 and is constructed to be mated with the conductive and conventional adhesives 306 and 309 to prevent the adhesives from adhering to a surface other than a patient's body when the electrode pad 300 is not in use.

In operation, the paper release sheet 314 does not adhere to the exposed surface 312 of the gripping pad 310 so that the gripping pad provides a non-sticky gripping edge for the user to manipulate the electrode pad. It will be noted that the gripping pad 310, as illustrated in FIG. 3, is mounted upon a first side 318 of the backing 302. As illustrated in FIG. 3, the gripping pad 310 is not centered along the first side 318 of the backing 302. The gripping pad 310 may be positioned anywhere along the first edge 318 of the backing 302.

Figure 3A:
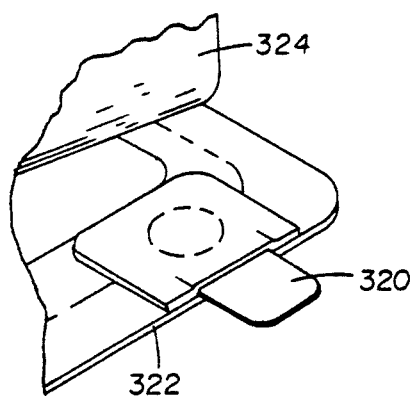
FIG. 3A is still another alternative embodiment of the electrode pad that is the subject of this invention.

With reference to FIG. 3A, a third embodiment of the invention is illustrated. Therein, a gripping tab 320 is fixedly mounted to a backing 322. A release sheet 324 is constructed to mate with the backing 322. Notably, the release sheet does not include a mating projecting portion as described above by reference to FIG. 1.

It will be appreciated that, although specific embodiments of the invention have been described herein for purposes of illustration, various modifications may be made without departing from the spirit and the scope of the invention. Accordingly, the invention is not limited except as by the appended claims.

I claim:

1. An electrode for conducting electricity between medical apparatus and the body of a patient, said electrode comprising:
    electrode pad means for conducting electricity to the body of the patient, said electrode pad means including an application surface having a periphery wherein a portion of said application surface includes electrode means for conducting electricity from said electrode pad means to the body of the patient, said electrode pad means further including adhesive means disposed upon said application surface of said electrode pad means for adhering said electrode pad means to the body of the patient, said electrode pad means including gripping means for providing a gripping edge to a user of the electrode, said gripping means including a gripping surface that is accessible to the user to provide the gripping edge; and
    release sheet means for covering said application surface of said electrode pad means to prevent said adhesive means from unintentionally sticking to objects other than the body of the patient, said release sheet means including means for substantially preventing said adhesive means from sticking to said release sheet means so that said release sheet means is easily removable from said electrode pad means, said release sheet means further including a tab portion constructed to extend beyond the periphery of said electrode pad means to provide an opposing gripping edge, opposite said gripping edge of said gripping means, to permit a user to remove said release sheet means from said electrode pad means.

2. The electrode as recited in claim 1 wherein said gripping surface of said gripping means is constructed of a material to substantially prevent said adhesive means of said electrode pad means from sticking to said gripping surface.

3. The electrode as recited in claim 1 wherein said gripping means further comprises a fixed portion and a projecting portion, said fixed portion being fixed to said electrode pad means and said projecting portion extending outward from said electrode pad means, said projecting portion including an exposed surface, said exposed surface including at least in part said gripping surface.

4. The electrode as recited in claim 1 wherein said electrode pad means further comprises first and second opposing edges, said gripping means being positioned on said first edge of said electrode pad means, said first edge being constructed of a first predetermined length, said release sheet means also including first and second opposing edges constructed to substantially mate with said first and second opposing edges of said electrode pad means, said tab portion of said release sheet means being positioned at said first edge of said release sheet means so that when said first and second edges of said release sheet means are mated with said first and second edges of said electrode pad means, said tab portion is positioned in mating relationship with said gripping means, said first edge of said release sheet having a length substantially equal to said first predetermined length of said first edge of electrode pad means.

5. The electrode as recited in claim 4 wherein said tab portion of said release sheet means is slightly larger than said projecting portion to project slightly beyond said gripping means.

6. The electrode as recited in claim 4 wherein said electrode pad means comprisés a substantially flexible backing upon which is mounted a substantially flexible electrode, the combination of said backing and said electrode making said electrode pad means substantially flexible.

7. The electrode as recited in claim 1 wherein said adhesive means further comprises a first electrically conductive adhesive disposed upon said electrode means of said electrode pad means, said first electrically conductive adhesive including an effective amount of a conductive material to enable electrical conduction between said electrode means and the body of the patient, said first electrically conductive adhesive further including an effective amount of an adhesive to adhere said electrode pad means to the body of the patient.

8. The electrode as recited in claim 7 wherein said first electrically conductive adhesive comprises a substantially conductive polymer.

9. The electrode as recited in claim 7 wherein said adhesive means further comprises a second conventional adhesive disposed upon said electrode pad means, said second conventional adhesive including an effective amount of a conventional adhesive for adhering said electrode pad means to the body of the patient.

10. The electrode as recited in claim 11 wherein said gripping means further comprises a fixed portion and a projecting portion, said fixed portion being fixed to said electrode pad means and said projecting portion extending outward from said electrode pad means, said projecting portion including an exposed surface, said exposed surface including at least in part said gripping surface.

11. The electrode as recited in claim 10 wherein said electrode pad means comprises a substantially flexible backing upon which is mounted a substantially flexible electrode, said substantially flexible backing and said substantially flexible electrode being constructed in a manner so that said electrode pad means is substantially flexible.

12. The electrode as recited in claim 11 wherein said gripping surface of said gripping means is constructed of a material to substantially prevent said adhesive means of said electrode pad means from sticking to said gripping surface.

13. The electrode as recited in claim 12 wherein said gripping surface comprises vinyl.

14. The electrode as recited in claim 12 wherein said release sheet means comprises a paper release sheet including a first surface adapted to be in contact with said first substantially conductive adhesive and said second conventional adhesive, said first surface of said paper release sheet being covered with an effective amount of wax to enable said release sheet means to be readily removable from said first substantially conductive adhesive and said second conventional adhesive of said adhesive means.

15. The electrode as recited in claim 14 wherein said backing of said electrode pad means comprises a foam backing.

16. The electrode as recited in claim 15 wherein said electrode of said electrode pad means comprises a metallic electrode.

17. An electrode for conducting electricity between medical apparatus and the body of a patient, said electrode comprising:

electrode pad means for conducting electricity between the medical apparatus and the body of the patient, said electrode pad means including a substantially flexible backing having an application surface having a periphery wherein a portion of said application surface includes a substantially flexible electrode for conducting electricity from said electrode pad means to the body of the patient, said electrode pad means further including adhesive means disposed upon said application surface of said electrode pad means for adhering said electrode pad means to the body of the patient, said electrode pad means further including conductor means for electrically coupling the medical apparatus to said substantially flexible electrode;

gripping means for providing a gripping edge to a user of the electrode, said gripping means including a first fixed portion fixed to said flexible backing of said electrode pad means, said gripping means further including a second projecting portion integral with said first portion and projecting outward from said flexible backing of said electrode pad means to provide the gripping edge to the user, said second projecting portion including a gripping surface comprising a material selected to substantially prevent said adhesive means of said electrode pad means from adhering to said gripping surface of said second projecting portion of said gripping means; and release sheet means for covering said electrode pad means to prevent said adhesive means from unintentionally sticking to objects other than the body of the patient, said release sheet means including means for substantially preventing said adhesive means from sticking to said release sheet means so that said release sheet means is easily removable from said electrode pad means, said release sheet means including a tab portion constructed to extend beyond the periphery of said electrode pad means to provide an opposing gripping edge, opposite said gripping edge of said gripping means to permit a user to remove said release sheet means from said electrode pad means.

18. The electrode as recited in claim 17 wherein said adhesive means further comprises a first electrically conductive adhesive disposed upon said substantially flexible electrode of said electrode pad means, said first electrically conductive adhesive including an effective amount of a conductive material to enable electrical conduction between said substantially flexible electrode and the body of the patient, said first electrically conductive adhesive further including an effective amount of an adhesive to at least partially adhere said electrode pad means to the body of the patient.

19. The electrode as recited in claim 18 wherein said first electrically conductive adhesive comprises a substantially conductive polymer.

20. The electrode as recited in claim 18 wherein said adhesive means further comprises a second conventional adhesive disposed upon said electrode pad means, said second conventional adhesive including an effective amount of a conventional adhesive for adhering said electrode pad means to the body of the patient.

21. The electrode as recited in claim 20 wherein said release sheet means comprises a paper release sheet including a first surface adapted to be in contact with said first substantially conductive adhesive and said second conventional adhesive, said first surface of said paper release sheet being covered with an effective amount of wax to enable said release sheet means to be readily removable from said first substantially conductive adhesive and said second conventional adhesive of said adhesive means.

22. The electrode as recited in claim 21 wherein said gripping surface of said second projecting portion of said gripping means comprises vinyl.

23. The electrode as recited in claim 21 wherein said substantially flexible backing of said electrode pad means comprises a foam backing.

24. The electrode as recited in claim 21 wherein said substantially flexible electrode of said electrode pad means comprises a metallic electrode.

25. The electrode as recited in claim 21 wherein said tab portion of said release sheet means is constructed and positioned to substantially mate with said second projecting portion of said gripping means and wherein said tab means is slightly larger than said second projecting portion to extend slightly beyond said second projecting portion.

26. An electrode pad for conducting electric signals between a patient and an electrical cable of a defibrillator, said electrode pad comprising:

a foam backing having a thickness selected to permit said foam backing to be substantially flexible, said foam backing having an application surface having a periphery of a first predetermined surface area;

a metallic electrode having a second predetermined surface area wherein said second predetermined surface area is smaller than said first predetermined surface area, said metallic electrode having a back surface and a conducting surface, said metallic electrode being mounted upon said application surface of said foam backing with said back surface of said metallic electrode proximate said application surface of said foam backing and positioned in a manner such that an adhesive portion of said application surface is exposed about the entire periphery of said metallic electrode, the thickness of said metallic electrode being selected to permit the combination of said metallic electrode and said foam backing to be substantially flexible, said metallic electrode being constructed to conduct electric signals to and from the patient by way of said conducting surface;

a connector mechanically coupled to said foam backing, said connector including an electrically conducting stem for electrically coupling said connector to said metallic electrode, said connector further including a receiving clip for mechanically connecting the electrical cable of the defibrillator to said electrically conducting stem of said connector thereby to electrically couple said metallic electrode to the defibrillator;

a first adhesive composed at least in part from a sufficient quantity of semiconducting polymer to render said first adhesive substantially electrically conductive, said first adhesive further including a sufficient amount of an adhesive to make said first adhesive removably adherable to the body of a patient, a first portion of said first adhesive being disposed over said conducting surface of said metallic electrode in sufficient quantity to removably adhere said metallic electrode to the body of the patient, a second portion of said first adhesive being disposed upon said adhesive portion of said application surface of said foam backing and about the periphery of said metallic electrode in a manner such that a periphery portion of said application surface is not covered by said second portion of said first adhesive, said periphery portion of said application surface being positioned about the periphery of said application surface of said foam backing;

a second adhesive disposed upon said periphery portion of said foam backing in sufficient quantity to adhere said periphery portion of said foam backing to the body of the patient;

a vinyl tab having a first mounted portion and a second projecting portion, said first mounted portion of said vinyl tab being mounted to said adhesive portion of said application surface of said foam backing such that said second projecting portion of said vinyl tab extends beyond the periphery of said foam backing to provide a gripping edge to a user of the electrode pad means, said projecting portion of said vinyl tab having first and second gripping surfaces each having a third predetermined surface area sufficient to permit said projecting portion to be gripped by the fingers of the user;

a reinforcing foam pad having a first surface and a second surface opposite said first surface, said reinforcing foam pad being mounted to said adhesive portion of said foam backing in a manner such that said first surface of said reinforcing foam pad is proximate said mounting portion of said vinyl tab and further such that said reinforcing foam pad substantially covers said first mounted portion of said vinyl tab, a portion of said second adhesive being disposed upon said second surface of said reinforcing pad; and a paper release sheet mounted upon said application surface of said foam backing and being positioned to mate with said foam backing, said paper release sheet having a first surface positioned proximate said first and second adhesives, said first surface of said paper release sheet being covered with a sufficient amount of wax to allow ready separation of said paper release sheet from said first and second adhesives, said paper release sheet including a tab portion constructed to extend beyond the periphery of said foam backing and to substantially mate with said projecting portion of said vinyl tab, said tab portion being slightly larger than said projecting portion to extend slightly beyond said projecting portion, thereby to provide a gripping edge operative in combination with said first and second gripping surfaces to allow said paper release sheet to be readily gripped and separated from said first and second adhesives.

* * * * *